(12) United States Patent
Takemoto

(10) Patent No.: US 9,581,584 B2
(45) Date of Patent: Feb. 28, 2017

(54) APPARATUS FOR MEASURING BLOOD CELLS AND IMMUNITY FROM WHOLE BLOOD

(71) Applicant: HORIBA, Ltd., Kyoto-shi, Kyoto (JP)

(72) Inventor: Kazumasa Takemoto, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 118 days.

(21) Appl. No.: 14/279,151

(22) Filed: May 15, 2014

(65) Prior Publication Data

US 2014/0341779 A1    Nov. 20, 2014

(30) Foreign Application Priority Data

May 16, 2013 (JP) .................................. 2013-104028

(51) Int. Cl.

| | |
|---|---|
| G01N 15/06 | (2006.01) |
| G01N 33/00 | (2006.01) |
| G01N 33/48 | (2006.01) |
| G01N 33/49 | (2006.01) |
| G01N 35/04 | (2006.01) |
| G01N 35/10 | (2006.01) |
| G01N 33/53 | (2006.01) |
| G01N 15/10 | (2006.01) |

(52) U.S. Cl.
CPC ....... *G01N 33/491* (2013.01); *G01N 33/5304* (2013.01); *G01N 35/04* (2013.01); *G01N 35/10* (2013.01); *G01N 35/1004* (2013.01); *G01N 2015/1006* (2013.01); *G01N 2035/0437* (2013.01); *G01N 2333/46* (2013.01)

(58) Field of Classification Search
CPC ......... G01N 15/06; G01N 33/00; G01N 33/48
USPC ..... 422/50, 68.1, 62, 63, 64, 65, 66, 67, 73, 422/81, 82, 82.01, 82.05, 501, 509, 510; 436/43, 518, 523, 533, 534, 535, 536, 47, 436/48, 49, 63, 66, 69, 823, 824
See application file for complete search history.

(56) References Cited

U.S. PATENT DOCUMENTS

| | | | |
|---|---|---|---|
| 4,030,888 A * | 6/1977 | Yamamoto et al. | ............. 422/67 |
| 4,997,769 A * | 3/1991 | Lundsgaard | .................... 436/66 |
| 5,789,252 A | 8/1998 | Fujita et al. | |

(Continued)

FOREIGN PATENT DOCUMENTS

| | | |
|---|---|---|
| CN | 1940560 A | 4/2007 |
| JP | 06207944 A | 7/1994 |

(Continued)

OTHER PUBLICATIONS

ISA European Patent Office, Extended European Search Report of EP14168557, Oct. 6, 2014, 9 pages.

(Continued)

*Primary Examiner* — Brian J Sines
(74) *Attorney, Agent, or Firm* — Alleman Hall McCoy Russell & Tuttle LLP

(57) ABSTRACT

A diluted cleaning solution is contacted with the inner wall surface of an immunity measuring cell every time an immunity measurement treatment of a specimen is performed. Therefore, a diluting liquid is injected in advance, then a cleaning solution is injected, whereby a diluted cleaning solution is produced in the immunity measuring cell. As a result, the inner wall surface of the immunity measuring cell is maintained in a preferable state and the interval of the routine cleanings can be prolonged.

5 Claims, 7 Drawing Sheets

(56) References Cited

U.S. PATENT DOCUMENTS

| | | | |
|---|---|---|---|
| 6,043,205 A * | 3/2000 | Hoshiko et al. | 510/161 |
| 6,106,778 A | 8/2000 | Oku et al. | |
| 6,146,592 A * | 11/2000 | Kawashima et al. | 422/67 |
| 6,197,255 B1 * | 3/2001 | Miyake et al. | 422/64 |
| 6,440,369 B1 * | 8/2002 | Oonuma et al. | 422/64 |
| 6,605,213 B1 * | 8/2003 | Ammann et al. | 210/222 |
| 7,250,303 B2 * | 7/2007 | Jakubowicz et al. | 436/54 |
| 8,062,591 B2 * | 11/2011 | Yamamoto | 422/63 |

FOREIGN PATENT DOCUMENTS

| | | |
|---|---|---|
| JP | H07333228 A | 12/1995 |
| JP | H09113516 A | 5/1997 |
| JP | 11108923 A | 4/1999 |
| JP | 2003226893 A | 8/2003 |
| JP | 3477352 B2 | 12/2003 |
| JP | 2004004098 A | 1/2004 |

OTHER PUBLICATIONS

State Intellectual Property Office of the People's Republic of China, Office Action Issued in Patent Application No. 201410200446.9, Oct. 18, 2016, 7 pages.

* cited by examiner

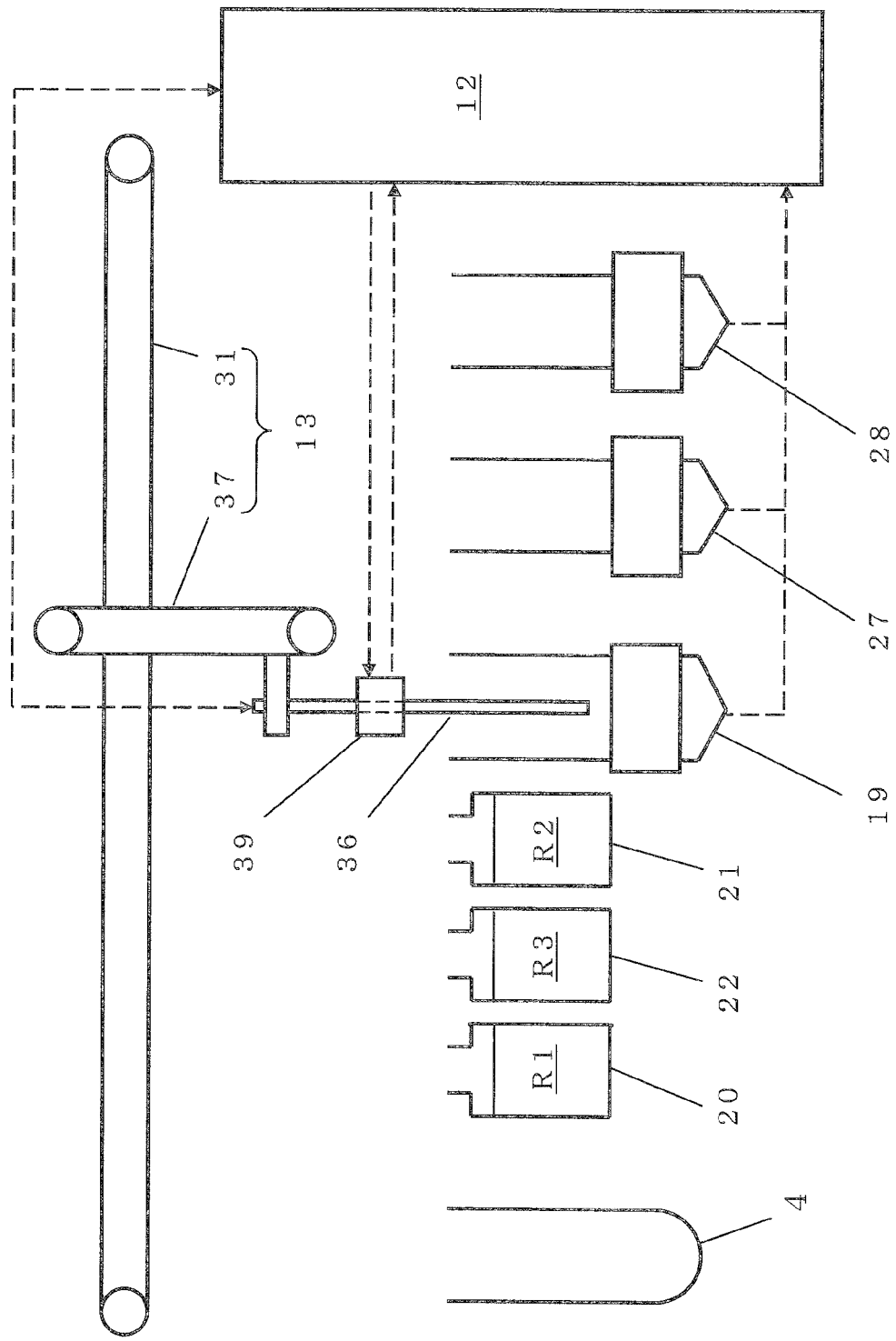

APPARATUS FOR MEASURING BLOOD CELLS AND IMMUNITY FROM WHOLE BLOOD

FIELD OF THE INVENTION

The present invention relates to an apparatus for measuring blood cells and immunity from whole blood, comprising an immunity measuring part that automatically measures the immunity of a blood specimen, and a blood cell counting-measuring part that automatically performs counting and measurement of blood cells.

BACKGROUND OF THE INVENTION

When an inflammatory reaction or tissue destruction has occurred in the body, it is diagnosed based on the detection of what is called an inflammatory marker as an index. One representative example of the marker is a C-reactive protein (hereinafter to be referred to as CRP). CRP is a serum protein secreted by the liver into the blood on affliction with autoimmune diseases such as rheumatoid arthritis, malignant tumor, primarily bacterial infectious diseases and the like. Therefore, CRP is known to show high values in patients with these diseases. However, since CRP values show high individual differences, it is a particularly useful index when observing the progression of the disease state of individual patients, rather than comparing against the standard value or the CRP values of others. CRP is generally measured immunologically by a method such as ELISA (Enzyme-Linked ImmunoSorbent Assay) and the like.

In the meantime, the left shift of white blood cells and an increase in the number of white blood cells occur in the early stages of inflammation. Therefore, it is clinically highly important to simultaneously measure not only CRP but also white blood cells.

The present inventors took note of the above-mentioned aspect and provided for the first time an apparatus for measuring blood cells and immunity from whole blood, which simultaneously enables measurement of white blood cell and CRP (JP-B-3477352, hereinafter to be referred to as patent document 1).

The apparatus described in patent document 1 is configured to classify white blood cells into 3 types. White blood cells can be divided into five kinds of cells: neutrophils, eosinophils, basophils, monocytes and lymphocytes. Of these, neutrophil, eosinophil and basophil are sometimes referred to collectively as granulocytes. In the apparatus for measuring blood cells and immunity from whole blood of the above-mentioned patent document 1, granulocytes, monocytes and lymphocytes are counted as white blood cells (i.e., classification into 3 types).

As shown in FIGS. 5(a), 5(b), and 6, in the apparatus for measuring blood cells and immunity from whole blood of the above-mentioned patent document 1, a specimen container 4 containing a specimen, a CRP cell 19, reagent containers (20, 21, 22) containing the reagents for CRP measurement, and blood cell counting-measuring cells (WBC cell 27 for white blood cells, RBC cell 28 for red blood cells) are aligned and disposed in a line in the horizontal direction. A single sampling nozzle 36 is controlled to move in the horizontal direction (positioning movement above each container and cells) and downward and upward movements (movements to go into and out from each container and cells) in a predetermined order. The sampling nozzle 36 is a thin and long tube also called a "needle".

The processing steps and the order of movement of the sampling nozzle for the measurement of CRP and counting-measurement of blood cells are as shown in the flow chart of FIG. 7.

By these configurations, various processing steps for one specimen, such as the steps of [suction and discharging of specimen and CRP reagents, CRP measurement in CRP cell, blood cell counting and measurement in WBC cell and RBC cell, cleaning processing of each cell, cleaning processing of the outside of the nozzle where necessary after each processing step, and final cleaning processing of the inside and outside of the nozzle after the final step] are performed sequentially and full-automatically, and the whole processing steps require about 4 minutes per one specimen to complete.

In addition to the processing steps as mentioned above for one specimen, conventional apparatuses for measuring blood cells and immunity from whole blood are programmed to automatically perform routine cleanings of the CRP cell (container constituted to measure CRP) every time a predetermined number of specimens are processed.

Routine cleanings of the CRP cell are necessary for the following reasons.

For CRP measurement, a latex reagent for immunity measurement (e.g., anti-human CRP sensitized latex immunoreagent) is dispensed in the cell to perform a latex coagulating method, particularly, for example, the latex immunonephelometry RATE method. The latex reagent is an R3 reagent contained in a reagent container 22 in the examples of FIG. 5(a)-FIG. 7. In this case, latex particles contained in the latex reagent also attach to the inner wall surface of the CRP cell. The latex particles accompanying CRP relatively firmly attach to the inner wall surface and, as the number of treated specimens increases, the amount of the latex particles deposited on the inner wall surface increases. As a result, permeation of irradiation light for the CRP measurement is prohibited, and accurate measurement results cannot be obtained. Therefore, routine cleaning of the CRP cell is necessary.

Conventionally, to obtain accurate results of optical measurement, routine cleanings are performed for every specimen number of 15.

For routine cleanings of the CRP cell, a cleaning solution containing a cleaning agent for the latex reagent is used, so that the latex particles adhered to the inner wall surface of the cell as mentioned above can be removed. The cleaning solution is contained in a cleaning solution tank in the apparatus, and supplied to the CRP cell through an exclusive piping at the time of the aforementioned routine cleanings.

When the routine cleanings are started, a diluting liquid to be supplied into the CRP cell for rinsing the inside of the cell at the last stage of every CRP measurement is discharged, the next CRP measurement is discontinued, the cleaning solution in the aforementioned tank is supplied as it is (i.e., as undiluted solution) until the inside of the cell is filled, and the inner wall surface of the cell is immersed in the cleaning solution. This immersion state is maintained for 1-2 minutes, and the cleaning solution is discharged. Injection of the diluting liquid into and discharge thereof from the cell is repeated 6 or 7 times to perform rinsing, and the cleaning solution is thoroughly removed by the diluting liquid to prevent any remainder thereof. In this case, not only a simple rinsing movement involving injecting and discharging a fresh diluting liquid, but also a stirring movement by repeatedly sucking a diluting liquid injected into the cell from the cell, injecting diluting liquid again into the cell, and sucking the diluting liquid again from the cell may be added.

By a series of movements mentioned above, one routine cleaning takes about 6 minutes.

Routine cleanings of the CRP cell are free of problems and preferable for general tests. However, in an institution where a large number of specimens need to be measured, it is one of the factors that decrease the daily through-put.

In the constitution of conventional apparatuses for measuring blood cells and immunity from whole blood, the interval of routine cleanings of the CRP cell (number of specimens processed between the cleanings) and the cleaning steps performed in a single routine cleaning are appropriate and essential, and there is no room for increasing the interval of the routine cleanings, or shortening the time of single routine cleaning.

The problem of the present invention is to provide an apparatus for measuring blood cells and immunity from whole blood, which is capable of increasing the interval of the routine cleanings of the CRP cell and even eliminating the routine cleanings.

SUMMARY OF THE INVENTION

The present invention has the following characteristics:

(1) An apparatus for measuring blood cells and immunity from whole blood, configured such that an immunity measurement is performed in an immunity measuring cell and counting and measuring of blood cells is performed in blood cell counting-measuring cell(s), the apparatus comprising: an immunity measuring part comprising the immunity measuring cell; a reagent container containing a latex reagent for the immunity measurement; reagent container(s) containing other necessary reagent(s) for the immunity measurement; and a blood cell counting-measuring part comprising the blood cell counting-measuring cell(s);

wherein the immunity measuring part, the reagent container(s) and the immunity measuring part are placed at predetermined positions, and wherein the apparatus is configured such that a single sampling nozzle moves to the predetermined positions to suck and discharge a specimen and the reagent(s), and an immunity measurement is performed in the immunity measuring cell and counting and measuring of the blood cells is performed in the blood cell counting-measuring cell(s), the apparatus further comprising:

a cleaning solution tank containing a cleaning solution and a cleaning agent for the aforementioned latex reagent;

wherein the apparatus is configured such that every time immunity measurement of one specimen is completed in the immunity measuring cell and the specimen is discharged, a predetermined amount of a diluting liquid is first injected into the immunity measuring cell and then a predetermined amount of the cleaning solution is injected into the immunity measuring cell, whereby the cleaning solution diluted to a predetermined concentration contacts an inner wall surface of the immunity measuring cell, and then, the diluted cleaning solution is discharged.

(2) The apparatus for measuring blood cells and immunity from whole blood of the above-mentioned (1), wherein a bottom part of the immunity measuring cell is provided with a discharge port for discharging a liquid in the cell, and electromagnetic selector valve(s) is(are) connected to the discharge port, and the apparatus is configured such that the above-mentioned cleaning solution is injected into the immunity measuring cell through the discharge port by an operation of the electromagnetic selector valve.

(3) The apparatus for measuring blood cells and immunity from whole blood of the above-mentioned (2), wherein the apparatus is configured such that the entire amount of the above-mentioned cleaning solution to be injected is divided into plural portions and injected into the immunity measuring cell a plurality of times.

(4) The apparatus for measuring blood cells and immunity from whole blood of any of the above-mentioned (1)-(3), further comprising:

a sampling nozzle cleaning device accompanying the sampling nozzle, which is configured to discharge a diluting liquid and to clean the outer surface of the nozzle with the diluting liquid.

(5) The apparatus for measuring blood cells and immunity from whole blood of any of the above-mentioned (1)-(4), comprising the configuration such that:

the above-mentioned cleaning solution is injected in 3 seconds or less into the immunity measuring cell in which the predetermined amount of the diluting liquid has been injected; then the contact of the above-mentioned cleaning solution diluted to the predetermined concentration with the inner wall surface of the immunity measuring cell is maintained for 1-5 seconds; and then the aforementioned diluted cleaning solution is discharged in 3 seconds or less.

BRIEF DESCRIPTION OF THE DRAWINGS

FIG. 5(a) is FIG. 2 of this document, and FIG. 5(b) is FIG. 3 of this document.

FIG. 6 schematically shows the configuration of the main part of the apparatus of patent document 1 shown in FIG. 5(a).

DETAILED DESCRIPTION OF THE INVENTION

Figure 7:
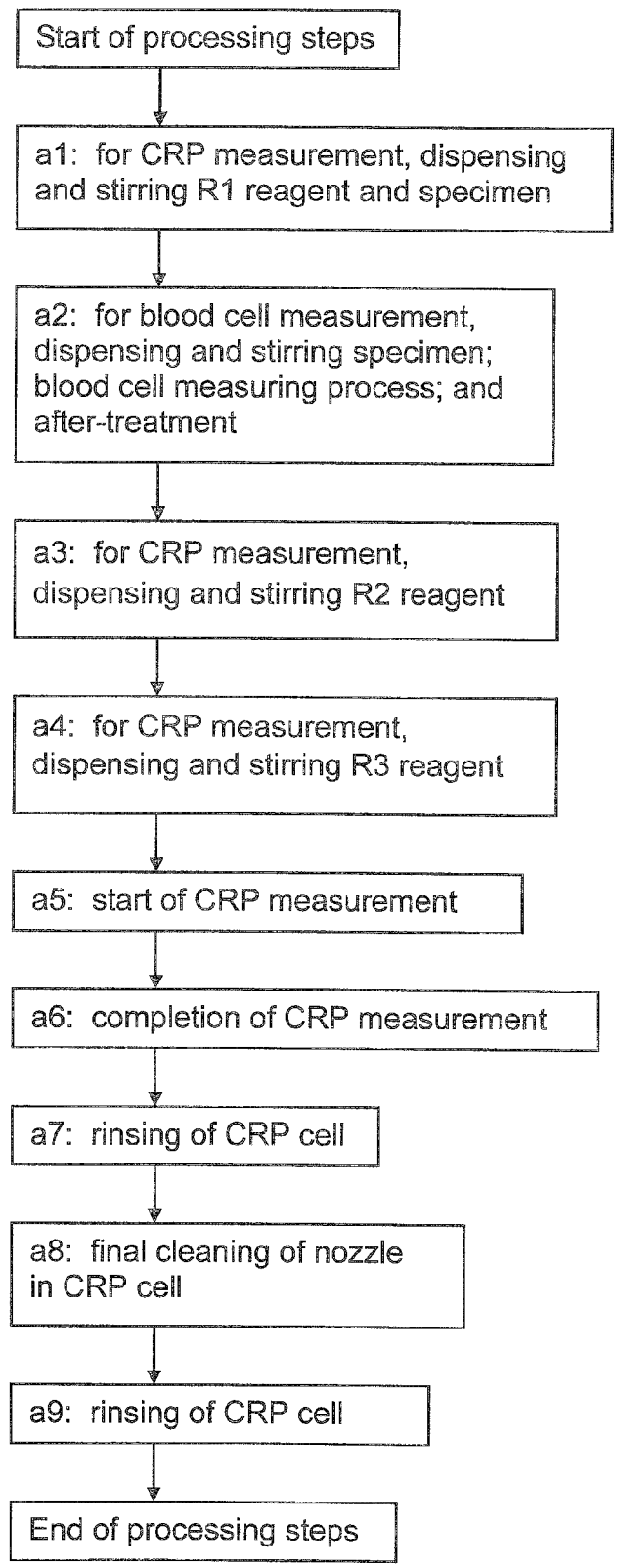
FIG. 7 is a flow chart showing the movement of the sampling nozzle in the apparatus shown in FIG. 5(a).

As in the steps a8, a9 in the flow chart of FIG. 7, the CRP cell is conventionally rinsed with a diluting liquid in the last stage of the treatment steps of the CRP measurement of each specimen.

While the process of conventional rinsing performed for every CRP measurement varies depending on the apparatus, for example, a simple process of rinsing involving repeats of filling the CRP cell with a diluting liquid discharged from a nozzle cleaning device (mentioned later) accompanying a sampling nozzle and discharging same, a process involving a stirring movement by repeating sucking a diluting liquid filled in the CRP cell with a sampling nozzle out from the cell, injecting same into the cell, and sucking the diluting liquid again out from the cell, and the like can be mentioned.

However, such rinsing of the CRP cell with a diluting liquid increases the amount of latex particles deposited on the inner wall surface as the number of specimen treatment increases, as mentioned in the above in the explanation of problems.

In the present invention, therefore, it was envisaged to bring a cleaning solution containing a cleaning agent for the latex reagent (hereinafter to be also referred to simply as "a cleaning solution"), which has been diluted to a predetermined concentration, in contact with the inner wall surface of an immunity measuring cell (CRP cell) only for a short time, after every immunity measurement (CRP measurement), namely, after immunity measurement (CRP measurement) of each specimen is completed and the specimen is discharged.

According to the studies by the present inventors, it was clarified that, when the inner wall surface of the CRP cell is excessively cleaned with a cleaning solution to eliminate latex particles, latex particles contributing to a CRP-latex coagulation reaction in the immunity measurement to be performed immediately thereafter also adhere to the inner wall surface of the CRP cell, which in turn inhibits the coagulation reaction and sometimes produces low CRP measurement values (false low value) of the value.

For example, when the following washings (a), (b) are performed, latex particles adhered to the inner wall surface of the CRP cell are completely removed or markedly decrease in number, and false low values are sometimes obtained in the CRP measurement to be performed immediately thereafter.

(a) Washing with a cleaning solution used for routine cleanings (namely, undiluted solution of the above-mentioned cleaning solution for latex reagent) instead of a diluting liquid, in a conventional washing step of the inner wall surface of the CRP cell.

(b) Long-time rinsing using a diluted cleaning solution, which is combined with stirring by bubbling and the like.

To prevent the above-mentioned false low value, prevent excessive prolongation of the treatment time for one specimen and increase the interval of the routine cleanings of the CRP cell, it was found preferable to maintain appropriate attachment of the latex particles to the inner wall surface of the CRP cell to stabilize the interface state of the inner wall surface.

Based on such new findings, for every CRP measurement in the present invention, a predetermined amount of a diluting liquid is injected into a CRP cell, and a predetermined amount of the aforementioned cleaning solution (undiluted solution) is injected thereinto to produce a diluted cleaning solution having a predetermined concentration (hereinafter to be also referred to as "diluted cleaning solution") in the CRP cell, rather than using the above-mentioned undiluted cleaning, the diluted cleaning solution is brought into contact with the inner wall surface of the CRP cell, the contact state is maintained for a predetermined short time, and the diluted cleaning solution is discharged, whereby the latex particles adhered to the inner wall surface of the CRP cell are appropriately removed. An injecting device such as a sampling nozzle cleaning device and the like may be used for the injection of a diluting liquid into the CRP cell.

When producing a diluted cleaning solution in the CRP cell, a predetermined amount of a diluting liquid is injected in advance into the CRP cell. Thus, an undiluted cleaning solution does not contact the inner wall surface of the CRP cell. As a result, latex particles are appropriately removed every time a CRP measurement is performed, and the latex particles appropriately remain on the inner wall surface of the CRP cell.

Since an appropriately diluted cleaning solution contacts the inner wall surface of the CRP cell in every CRP measurement, the interval of routine cleanings becomes strikingly long, or the routine cleanings are even eliminated, and the CRP measurement value does not show a false low value.

The configuration of the apparatus for measuring blood cells and immunity from whole blood of the present invention is explained in more detail in the following by referring to the Examples.

Figure 1:
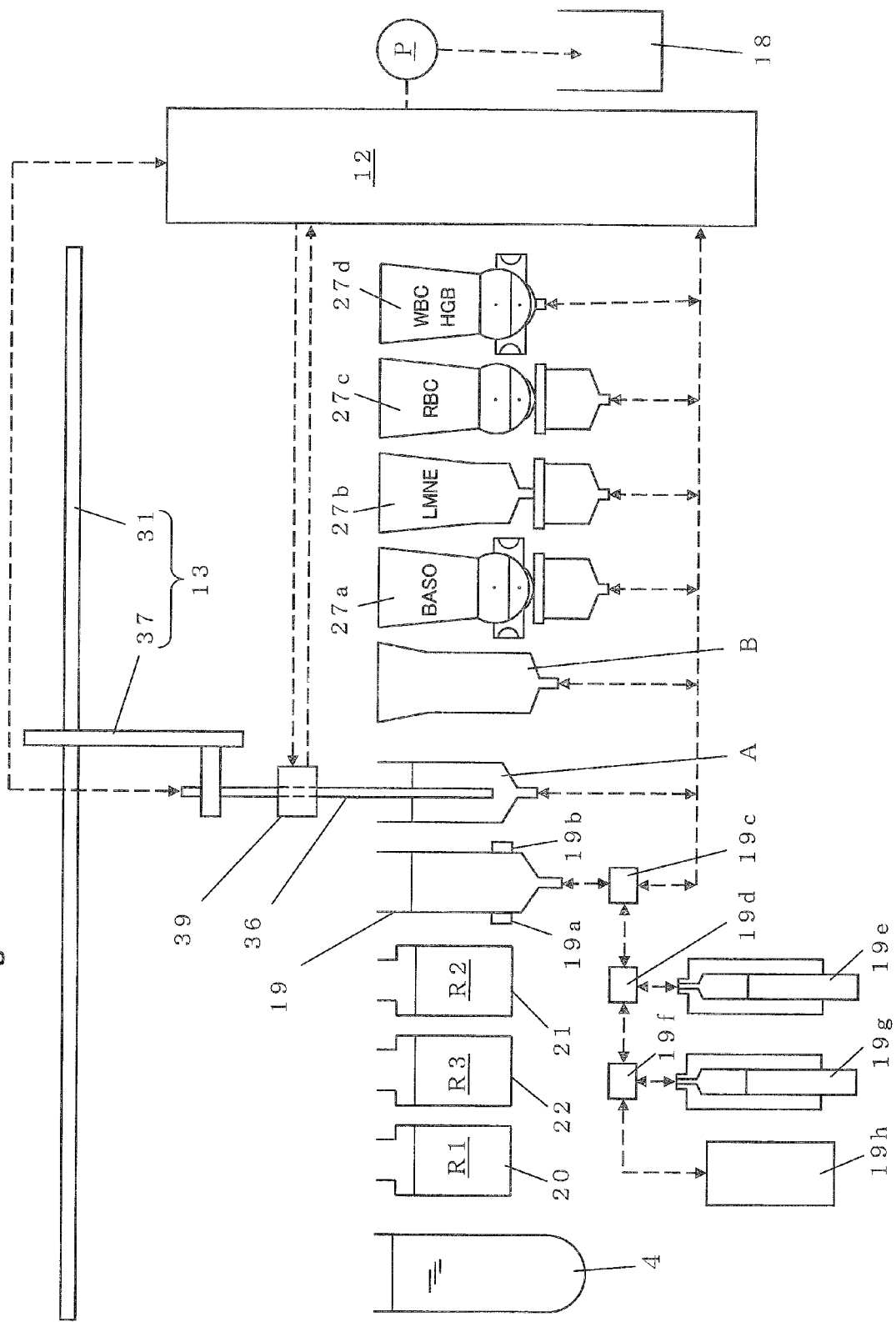
FIG. 1 schematically shows a configuration example of the main part of an embodiment of the apparatus for measuring blood cells and immunity from whole blood of the present invention.

FIG. 1 is a partially-enlarged view showing the characteristic configuration part in a preferable embodiment of the apparatus for measuring blood cells and immunity from whole blood of the present invention. As shown in the Figure, the apparatus comprises an immunity measuring part containing an immunity measuring cell 19, reagent containers (20, 21, 22) containing reagents for immunity measurement (R1, R2, R3), respectively, and a blood cell counting-measuring part containing blood cell counting-measuring cells (BASO cell 27a, LMNE cell 27b, RBC cell 27c, WBC cell 27d), in which blood cell counting, hemoglobin concentration measurement and the like are performed, which are disposed at predetermined positions. These measuring-cells form an embodiment preferable for detailed analyses including classification of white blood cells into 5 types. These measuring-cells are explained later.

In the embodiment of FIG. 1, a specimen container 4 containing a specimen is set at a predetermined position in the apparatus, and the predetermined positions of the specimen container 4, reagent containers (20, 22, 21), immunity-measuring cell 19 and blood cell counting-measuring cells (BASO cell 27a, LMNE cell 27b, RBC cell 27c, WBC cell 27d) are aligned along a straight line extending in the horizontal direction. A single sampling nozzle 36, that moves in the horizontal direction and the vertical direction by the action of a probe unit 13, moves along the straight line or downwardly or upwardly to enter into or go out from each container and each cell, along which to suck or discharge the specimen or reagent. Such an operating configuration is controlled by a computer. A sampling nozzle cleaning device 39 accompanying the sampling nozzle 36 is configured to discharge a diluting liquid which washes the outer surface of the sampling nozzle. It is configured so that the immunity measurement is automatically performed by the immunity-measuring cell 19 and the control part (not shown), and the counting and measurement of blood cells are automatically performed by the blood cell counting-measuring cells (27a-27d) and the control part.

Since FIG. 1 is a schematic drawing, each cell and container such as a chamber and the like is depicted to have a corner in the bottom. However, actually, they preferably have appropriate roundness in consideration of the smooth outflow and inflow of the liquid.

An important feature of the present invention is, as explained in the above-mentioned effect of the Invention, that a diluted cleaning solution having a predetermined concentration is produced in an immunity measuring cell 19 every time an immunity measurement of one specimen is completed in the immunity measuring cell 19 and the specimen is discharged (i.e., on completion of each immunity measurement), and the diluted cleaning solution is contacted with the inner wall surface of the immunity measuring cell 19.

The apparatus of the present invention includes a cleaning solution tank 19h containing the aforementioned undiluted cleaning solution containing a cleaning agent for the latex reagent, and also a tank containing a diluting liquid. The details of the cleaning solution are mentioned below.

A predetermined amount of a diluting liquid is first injected into the immunity measuring cell 19, and then, a predetermined amount of a cleaning solution (undiluted solution) is injected from a cleaning solution tank to produce a diluted cleaning solution in the immunity measuring cell. While the diluting liquid may be injected from a given injecting device through an exclusive piping, injection utilizing discharge from a sampling nozzle cleaning device (injection from an upper opening of the immunity measuring cell) is a preferable embodiment. The diluted cleaning solution is maintained for a predetermined time in the immunity measuring cell (namely, the diluted cleaning solution is contacted with the inner wall surface of the immunity measuring cell for a predetermined time) and then discharged. The order of movement is controlled by a control part.

By the above-mentioned process, a diluted cleaning solution is produced in the immunity measuring cell, and contacted with the inner wall surface of the immunity measuring cell every time the immunity measurement is completed, whereby the inner wall surface has latex particles appropriately adhered thereto, a false low value of the immunity measurement results is prevented, and the interval of routine cleanings can be increased. Under most appropriate conditions, routine cleanings become unnecessary. Furthermore, since the diluting liquid is first injected into the immunity measuring cell, the cleaning solution (undiluted solution) does not directly contact the inner wall surface of the cell, whereby excessive cleaning of the inner wall surface of the cell can be prevented.

Figure 3:
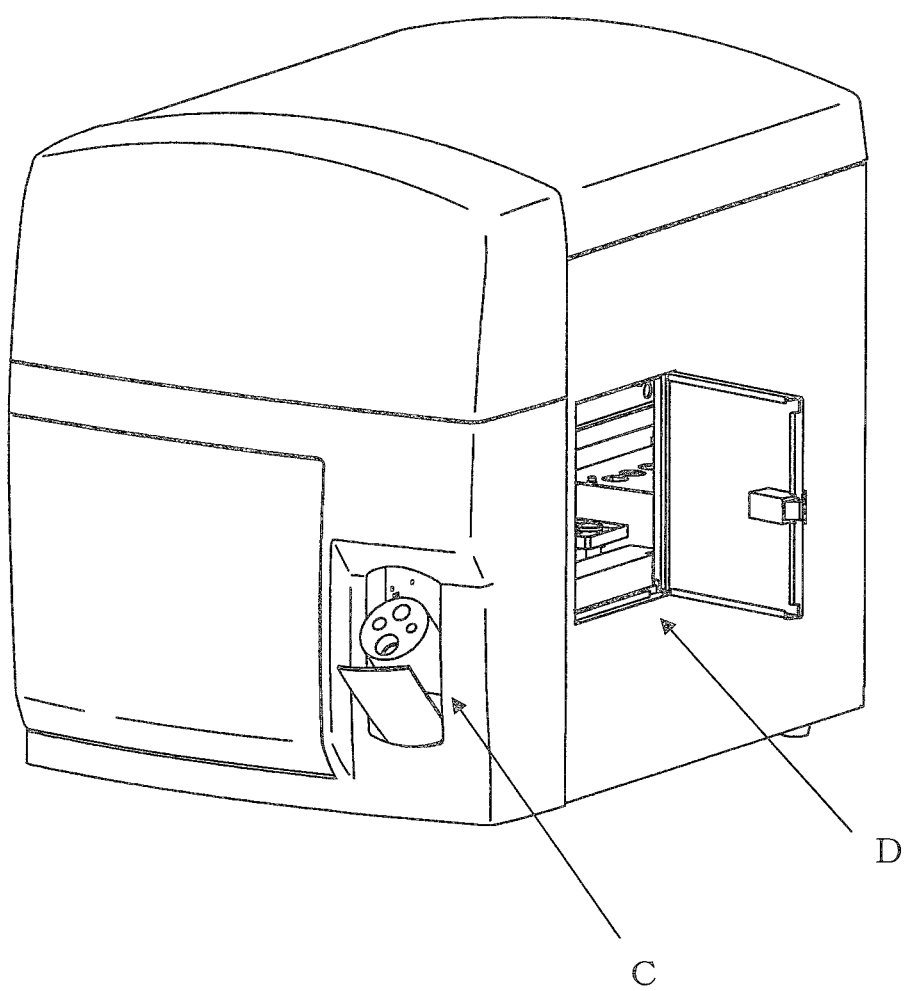
FIG. 3 shows one example of the appearance of the apparatus for measuring blood cells and immunity from whole blood of the present invention.

While the general appearance of the present apparatus for measuring blood cells and immunity from whole blood is not particularly limited, for example, one shown in FIG. 3 can be mentioned. In the embodiment of FIG. 3, a specimen container set part (blood collecting tube holder) C for setting a specimen container (also referred to as a blood collecting tube) containing a specimen is openably/closably provided on the front face. In addition, door D is provided on the side face to expose a part holding the reagent containers for immunity measurement, which enables supplementation of the reagents and maintenance of the immunity measuring part.

The techniques of conventionally-known whole blood cell immunity measuring apparatuses, blood cell counting and measuring apparatuses and immunity measuring apparatuses such as the above-mentioned patent document 1 and the like may be referred to for the basic configuration, mechanism, control, and measurement techniques necessary for placing the immunity measuring part and the blood cell measuring part at predetermined positions, moving the sampling nozzle in a controlled manner, performing suction and discharge of specimens and reagents, and further, automatically performing immunity measurement and blood cell counting and measuring in each cell. As a control part for controlling the mechanism of each part and processing the obtained data, a computer is appropriate.

The immunity measurement according to a latex coagulating method, such as the latex immunonephelometry RATE method, to be performed by the present apparatus, only needs to be an immunological measurement such as an analysis of components in blood plasma and the like, and is not particularly limited. Particularly, the measurement of CRP values is frequently used as a representative inflammatory marker in clinical laboratory tests (bacterial infections, etc.), and is an important measurement item for an apparatus for measuring blood cells and immunity from whole blood.

In the following explanation, the present invention is explained by referring to CRP measurement as an actual example of immunity measurement.

[Immunity Measuring Part (CRP Measuring Part)]

In the embodiment shown in FIG. 1, an immunity-measuring cell 19 is a cell configured to be able to measure CRP, which is provided with a light-irradiation part 19a and a light detection part 19b for the CRP measurement at the lower wall surfaces of the cell, and configured to be able to appropriately stir the liquid contained inside. In the following, the immunity-measuring cell is also referred to as the CRP cell.

In the CRP cell, the prior art may be referred to for the technique of optically measuring CRP according to a latex coagulating method, particularly, for example, the latex immunonephelometry RATE method, arrangement and structures of the elements in the light-irradiation part and the light detection part, material of the cell, and the configuration of the cell suitable for the measurement of CRP such as the shape, size and the like thereof. In FIG. 1, a configuration containing a light-irradiation part 19a and a light detection part 19b disposed to face each other is suggested.

In the embodiment of FIG. 1, a discharge port for discharging the liquid in the cell is provided at the bottom part of the CRP cell 19. To the discharge port is connected an electromagnetic selector valve 19c for pathway switching by a piping shown with a broken line. By the switching action of the electromagnetic selector valve 19c, a waste liquid is delivered to a waste liquid container 18, through the electromagnetic selector valve 19c and an electromagnetic valve device 12, by pump P.

In addition, the electromagnetic selector valve 19c is further connected with the second electromagnetic selector valve 19d, and the electromagnetic selector valve 19d is connected with a quantitative discharger (syringe) 19e for stirring the inside of the CRP cell. The liquid in the CRP cell is stirred by the formation of a pipeline by the switching action of electromagnetic selector valves 19c, 19d, and the sucking and discharge movements of the quantitative discharger 19e.

Furthermore, the second electromagnetic selector valve 19d is connected with the third electromagnetic selector valve 19f, and the electromagnetic selector valve 19f is connected with a quantitative discharger 19g and a cleaning solution tank 19h for injecting a cleaning solution into the CRP cell. First, a cleaning solution in the cleaning solution tank 19h is sucked into the quantitative discharger 19g by the formation of a sucking pipeline by the switching action of the third electromagnetic selector valve 19f and the sucking action of the quantitative discharger 19g. Then, a cleaning solution in the quantitative discharger is injected into the CRP cell by the formation of an injecting pipeline by the switching action of the electromagnetic selector valves 19*c*, 19*d*, 19*f* and the discharge action of the quantitative discharger 19*g*.

A reagent container 20 for the CRP measurement contains a hemolysis reagent (hereinafter to be referred to as R1 reagent). The R1 reagent may be known and, for example, a solution thereof a surfactant (synthesized substance or natural product such as saponin) as a main component and the like can be mentioned.

A reagent container 21 contains a buffer liquid (hereinafter to be referred to as R2 reagent). The R2 reagent may also be known and, for example, Tris-HCl (Tris-hydrochloric acid) buffer liquid, glycine buffer liquid and the like can be mentioned.

A reagent container 22 contains a latex reagent (hereinafter to be also referred to as R3 reagent). R3 reagent is produced by immobilizing the CRP antibody on the surface of the latex particles. The R3 reagent only needs to be a reagent usable for immunity measurement (CRP measurement in this example) according to the latex coagulating method, such as the latex immunonephelometry RATE method, for example, latex suspension sensitized with anti-human CRP rabbit polyclonal antibody, latex suspension sensitized with anti-human CRP mouse monoclonal antibody, latex suspension sensitized with anti-human CRP goat polyclonal antibody and the like can be mentioned.

Examples of the material of the latex particles include polystyrene latex and the like. A general particle size of the latex particles is about 0.01 μm-2 μm.

In a preferable embodiment, these reagent containers are configured to be collectively opened/closed by a lid that swings in the upward and downward directions by an actuator such as a solenoid, stepping motor and the like.

In a preferable embodiment, moreover, the reagent containers 21, 22 are contained in a cooling box provided with an electronic cooler composed of a Peltier element.

[Blood Cell Counting-Measuring Part]

While the measurement items of blood cells to be performed in the blood cell counting-measuring part are not particularly limited, for example, they may be counting of red blood cells (volume and frequency distribution), measurement of hemoglobin amount, classification of white blood cells into 3 types (counting of monocytes, lymphocytes and granulocyte fractions) as in patent document 1, or classification of white blood cells into 5 types (classification and counting of lymphocytes, monocytes, neutrophils, eosinophils, and basophils) may be further performed as in the embodiment shown in FIG. 1 of the present invention. These measurement items can be appropriately determined according to the object of the apparatus, demand of the user, cost of the product and the like.

A device for counting and measuring blood cells has a configuration to be operated by a control part, in each blood cell counting-measuring cell, which is necessary for performing the electric resistance method (also called an impedance method) and the optical measurement method according to the measurement items.

For example, WBC (number of white blood cells), RBC (number of red blood cells), PLT (number of platelets), MCV (volume of red blood cells), and Hct (hematocrit value) are measured by the electric resistance method as in the apparatus of patent document 1, and Hgb (hemoglobin concentration) and the like may be measured by absorption spectrophotometry in colorimetry (non-cyanogen method).

In the apparatus of patent document 1, the WBC/Hgb blood cell counting-measuring cell contains a measurement electrode pair for measuring WBCs based on the electric resistance method and a light-irradiation part and a light-receiving part for measuring Hgb. The RBC/PLT blood cell counting-measuring cell contains a measurement electrode pair for measuring RBC and PLT based on the electric resistance method.

In the embodiment shown in FIG. 1 of the present invention, the blood cell counting-measuring cells provided as blood cell counting-measuring parts are BASO cell 27*a*, LMNE cell 27*b*, RBC cell 27*c*, and WBC cell 27*d*.

BASO cell 27*a* is a cell for counting basophils, wherein blood cells other than basophils are hemolyzed or contracted by the action of a reagent to leave only the basophils to be counted, and the basophils are counted by the electric resistance method.

LMNE cell 27*b* is a cell configured to count lymphocytes (L), monocytes (M), neutrophils (N), and eosinophils (E) by the below-mentioned light-focused flow impedance method.

RBC cell 27*c* is a cell configured to count red blood cells and platelets and, like the RBC/PLT blood cell counting-measuring cell in the apparatus of patent document 1, an aperture and electrodes are provided on the lower part of the cell so that the electric resistance method can be performed.

WBC cell 27*d* is similar to the WBC/Hgb blood cell counting-measuring cell in the apparatus of patent document 1, and provided to more accurately count white blood cells. WBC cell can count whole leukocyte, including lymphocytes, monocytes, neutrophils, eosinophils, and basophils, by using an exclusive reagent, and includes a measuring apparatus having an aperture and electrodes to perform the impedance method. In this cell, the hemoglobin concentration is also measured besides counting of the white blood cells.

In an electrical resistance method, a sample liquid made of a blood specimen dispersed in a diluting liquid is introduced into a flow channel provided with an aperture (small opening) like an orifice, which has a reduced cross-sectional area, and an aperture is interposed between a pair of electrodes, and the volume of a particle passing through the aperture is measured based on the changes of the electrical characteristics between the electrodes.

On the other hand, a preferable optical technique for identifying a blood cell is flow cytometry. According to this technique, a predetermined irradiation light is irradiated as a beam light focused on the blood cells in a sample liquid advancing through a flow channel, and the blood cells are distinguished from optical characteristics such as light scattering, light absorbance and the like resulting therefrom.

A method involving flow cytometry and the electric resistance method to be performed at the same time (light-focused flow impedance method) is a preferable method for classifying white blood cells into 4 types (obtaining an LMNE matrix). In the embodiment of the present invention shown in FIG. 1, a flow channel for the light-focused flow impedance method, and a light irradiating device, a light receiving device and an electrode pair therefor are provided in the LMNE cell 27*b*, whereby the data for classifying white blood cells into 4 types (data pairs for each blood cell [volume, absorbance]) can be obtained.

The count results of blood cells are appropriately processed in the control part, and displayed as a scattergram such as an LMNE matrix, or histogram and the like.

The conventionally-known techniques may be referred to for each device configuration necessary for performing the electric resistance method, flow cytometry, and light-focused flow impedance method.

[Sampling Nozzle and Driving Mechanism Therefor]

In the embodiment shown in FIG. 1, a specimen container 4, reagent containers 20, 22, 21, CRP cell 19, cleaning chamber A for immunity measurement, and blood cell counting-measuring cells (27a, 27b, 27c, 27d) are placed at predetermined positions. By this arrangement, a sampling nozzle (hereinafter to be also referred to as "nozzle") moves to each, predetermined position as well as downwardly and upwardly, thus enabling suction and discharge of the specimen and reagents. Since the moving route of the nozzle and the mechanism of the probe unit are not complicated, and rapid processing is possible, respective predetermined positions that are preferably aligned and placed in one line as in FIG. 5(b) are preferable.

A nozzle is also called a needle, and is a long and thin pipe used for suction and discharge of specimens and reagents by inserting the tip thereof into each container and cell. The back-end of a nozzle is connected by piping to a sucking-discharging pump via an electromagnetic valve.

The conventionally-known techniques such as patent document 1 and the like may be referred to for the mechanism of a probe unit 13, which horizontally moves the nozzle along a predetermined pathway, as well as downwardly and upwardly. Examples thereof include a rectilinear mechanism using a timing-belt (or V-belt), which has a shape of an endless belt (looped belt) and the like, a rectilinear mechanism by a ball screw, a rectilinear mechanism by a cylinder, a rectilinear mechanism by other actuator, a moving mechanism by a driving arm, which is a combination of these, and the like.

Figure 5A:
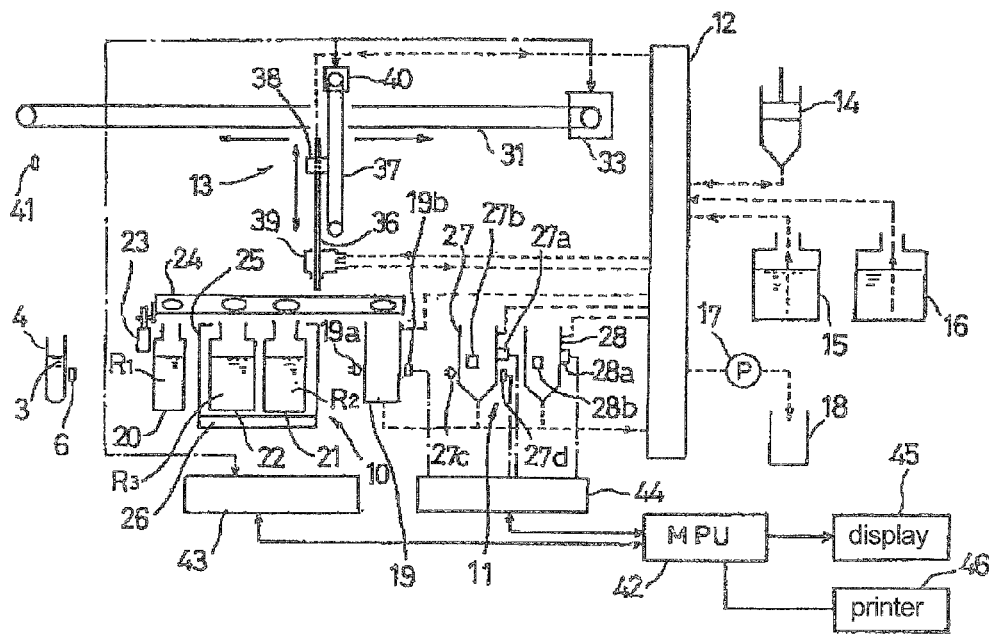
FIGS. 5(a) and 5(b) show the configuration of the apparatus described in patent document 1.
Figure 5B:
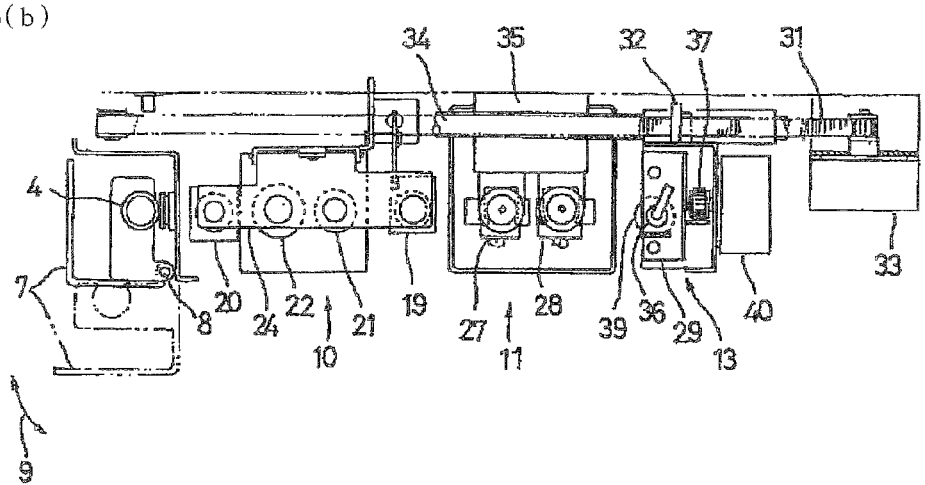

In the embodiment shown in FIG. 1, the nozzle can move in the horizontal direction and the vertical direction in the same manner as in FIG. 5(a), by the timing belt 31 in the horizontal direction and the timing belt 37 for the upward and downward directions.

The nozzle reciprocates almost right above the reagent containers and cells aligned and placed on a straight line, and descends or ascends at predetermined positions to perform sucking and discharge of specimens and reagents, and washing or cleaning. Such movements are controlled by a computer and performed as programmed.

A nozzle cleaning device 39 accompanies the nozzle 36.

The nozzle cleaning device has an annular-shaped main part, and the nozzle passes through the central through-hole thereof (the tip of the nozzle is located below the nozzle cleaning device).

The nozzle cleaning device 39 moves in the horizontal direction along with nozzle 36, and fixed at a certain height in the vertical direction. Therefore, when nozzle 36 moves downwardly and upwardly, the annular-shaped main part of the nozzle cleaning device 39 relatively moves on the outer surface of the nozzle.

In a preferable embodiment, when the nozzle moves to the lowest part, a diluting liquid is discharged from the annular-shaped main part of the nozzle cleaning device, whereby the whole outer peripheral surface of the nozzle is washed.

[Cleaning of the CRP Cell with Diluted Cleaning Solution]

The CRP cell is cleaned with a diluted cleaning solution (contact of diluted cleaning solution with inner wall surface) in each CRP measurement of one specimen.

The CRP cell is preferably cleaned with a diluted cleaning solution after rinsing the CRP cell, which is performed after discharge of a mixture of the sample liquid and the reagent on completion of the measurement of the inner wall surface of the CRP cell, namely, after completion of all processing steps in the CRP cell.

In the conventional flow chart shown in FIG. 7 as an example, the CRP cell is rinsed in step a9 at the end of the treatment steps. In such processing steps, it is preferable to clean the CRP cell with a diluted cleaning solution after step a9, and thereafter rinse the CRP cell with a diluting liquid.

A cleaning solution (undiluted solution) usable in the present invention only needs to contain the above-mentioned cleaning agent for the latex reagent. Examples of cleaning agents for the latex reagent include the following.

surfactants such as Brij (polyoxyethylenelauryl ether surfactant), Triton (polyoxyethylenealkylphenylether surfactant), Tween (polyoxyethylenesorbitan surfactant) and the like organic chelating agents such as ethylenediaminetetraacetic acid (EDTA) and the like acids such as citric acid, phosphoric acid, hydrochloric acid and the like.

proteases such as Savinase (manufactured by Novozymes) and the like.

The composition of a cleaning solution (undiluted solution) for general latex reagents is obtained by dissolving a cleaning agent as mentioned above in a solvent such as pure water, ethanol and the like.

While the content of the cleaning agent in the cleaning solution (undiluted solution) (i.e., concentration of cleaning agent in the undiluted solution) varies depending on the combination of the cleaning agent and the diluting liquid, it is preferably about 0.01 wt %-2.0 wt %, more preferably 0.5 wt %-1.0 wt %.

The aforementioned cleaning solution can be obtained as a commercially available cleaning solution such as Minozyme 5D, Minozyme Plus and the like.

In the present invention, it is important to inject only a predetermined amount of a diluting liquid into a CRP cell from a sampling nozzle cleaning device, then inject only a predetermined amount of a cleaning solution to contact a diluted cleaning solution having a predetermined concentration to the inner wall surface of the cell.

To obtain a diluted cleaning solution, the amount of the diluting liquid to be injected into the CRP cell earlier, and the amount of the cleaning solution to be injected later can be appropriately determined according to the volume of the CRP cell to be filled, and the concentration of the object diluted cleaning solution.

The content ratio of the cleaning solution (undiluted solution) in the diluted cleaning solution is preferably 30 wt %-60 wt %, more preferably 40 wt %-50 wt %.

When latex particles tend to deposit on the inner wall surface of the CRP cell (when the permeation amount of irradiation light for CRP measurement tends to decrease) due to the difference in the cleaning effect resulting from the kind of the cleaning solution, the degree of dilution may be adjusted, and the concentration of the cleaning agent may be increased. Conversely, when the latex particles on the inner wall surface of the CRP cell tend to be removed too much (propensity toward false low values), the degree of dilution may be adjusted, and the concentration of the cleaning agent may be decreased.

The amount of the diluted cleaning solution to be injected into the CRP cell (total of diluting liquid and cleaning solution) is preferably an amount that renders the liquid surface of the diluted cleaning solution the same as or above the height of the light path from an irradiation light source for the CRP measurement to the light emitting element.

In a preferable embodiment of the present invention, a cleaning solution is injected in a short time into a CRP cell, into which a diluting liquid has already been injected, the injection completion state is maintained for a predetermined time, and then the cleaning solution is discharged in a short time. These movements are performed by controlling with pumps and valves.

The cleaning solution is preferably injected in not more than 3 seconds, more preferably 1-2 seconds. When the time necessary for injection is too long, the inner wall surface is excessively cleaned. When the time necessary for injection is shortened by strongly injecting the cleaning solution, problems occur since the cleaning solution splashes due to strong injection and the like.

After completion of the injection of the cleaning solution, the injection completion state is preferably maintained for 1-5 seconds, more preferably 1-2 seconds. While the time of contact of the diluted cleaning solution with the inner wall surface of the CRP cell is preferably adjusted by the maintenance time, it should be taken into consideration that the diluted cleaning solution is also in contact with the inner wall surface of the CRP cell during injection and discharge.

The diluted cleaning solution is preferably discharged in not more than 3 seconds, more preferably not more than 2 seconds, and preferably discharged in the shortest possible time.

By contacting the diluted cleaning solution with the inner wall surface of the immunity measuring cell for only an extremely short time as mentioned above, the inner wall surface maintains latex particles appropriately adhered thereto, prevents the immunity measurement result from being a false low value, and can increase the interval of routine cleanings. Under most appropriate conditions, routine cleanings become unnecessary.

When the cleaning solution injection time, time of maintaining the injection completion state, and discharge time are longer than the above-mentioned ranges, the amount of the latex particles on the inner wall surface becomes excessively small, a false low value may be produced, and the treatment time of one specimen unpreferably becomes too long. On the other hand, when the time of maintaining the injection completion state is shorter than the above-mentioned range, the latex particles are deposited on the inner wall surface as the specimen measurement proceeds, and routine cleaning of the inner wall surface of the CRP cell becomes necessary, though not as frequently as in the conventional methods.

When latex particles tend to deposit on the inner wall surface of the CRP cell (when the permeation amount of irradiation light for CRP measurement tends to decrease) due to the difference in the cleaning effect resulting from the kind of the cleaning solution and dilution concentration, the contact time with the inner wall surface may be extended. Conversely, when the latex particles on the inner wall surface of the CRP cell tend to be removed too much (propensity toward false low values), the contact time with the inner wall surface may be shortened.

As mentioned above, important adjustment parameters, when a diluted cleaning solution is contacted with the inner wall surface of the CRP cell, are the concentration of a diluted cleaning solution and the contact time of a diluted cleaning solution. To achieve the object of the present invention, these two parameters need to be adjusted in a mutually related manner and, when the concentration is increased, the contact time should be shortened, and when the concentration is decreased, the contact time should be prolonged.

The important feature of the present invention is that the state of the inner wall surface of the CRP cell (latex particle deposition state) after every CRP measurement is maintained constant by contacting a diluted cleaning solution having a predetermined concentration with the inner wall surface of the CRP cell for a predetermined time after every CRP measurement. To maintain the state of the inner wall surface at a constant level, the above-mentioned concentration of the diluted cleaning solution and the above-mentioned contact time of the diluted cleaning solution are appropriately selected and combined and, where necessary, the concentration may be slightly increased/decreased, and the contact time may be slightly increased/decreased within the above-mentioned ranges. However, when the concentration of the diluted cleaning solution is increased, even a small difference in the contact time leads to a marked difference in the results, which makes it difficult to control the movements relating to time. On the contrary, when the concentration of the diluted cleaning solution is decreased, every contact time becomes long, and the number of treated specimens decreases. When the concentration is increased/decreased, and the contact time is slightly increased/decreased, the above points should be taken into consideration. It is also preferable to adjust the amount to be increased/decreased in the concentration and the contact time also in consideration of the consumption amount of the cleaning solution, inconsistent cleaning effect due to various discharge rates, and the time necessary for cleaning, so that an appropriate cleaning effect can be obtained and the time necessary for cleaning will not be too long.

While the pathway employed for injecting a cleaning solution into the CRP cell is not particularly limited, a constitution wherein electromagnetic selector valves 19c, 19d, 19f are connected to a discharge port of the CRP cell 19, and a cleaning solution in a cleaning solution tank 19h can be injected into the CRP cell 19 from the discharge port by the switching action of these electromagnetic selector valves and the quantitative discharger 19g, as shown in the explanation of discharge port in FIG. 1, is preferable.

By injecting a cleaning solution from the lower side of the CRP cell, a pipeline for stirring which is connected to a discharge port of the CRP cell (pipeline from electromagnetic selector valve 19d to the CRP cell via electromagnetic selector valve 19c) can be cleaned with an undiluted cleaning solution. In addition, by injecting a cleaning solution from the lower side of the CRP cell, into which a diluting liquid has been injected in advance, the cleaning solution can be injected and stirred at the same time.

As mentioned above, when a cleaning solution is injected into the CRP cell from the discharge port at the lower side and the total injection volume is injected at once in a short time, the cleaning solution may spout upward due to the pressure drop and splash from the upper opening of the CRP cell. This is because a high pressure tends to act on the stirring line during the injection of the cleaning solution, since the inner diameter of the piping in the stirring line at the lower side of the CRP cell is smaller than that of the piping for injecting the cleaning solution. Therefore, the injection of the cleaning solution is preferably divided into plural portions (2-4 portions, preferably 3 portions) and injected a plurality of times (2-4 times, preferably 3 times).

Now a preferable embodiment capable of shortening the measurement processing time necessary for one specimen is explained.

When CRP measurement is performed, latex particles attach not only to the inner wall surface of the CRP cell but also to the outer surface and inner surface of the sampling nozzle. While the above-mentioned patent document 1 does not explicitly state, conventionally, the nozzle with latex particles adhered thereto after completion of all CRP measurements is finally cleaned (sufficient cleaning including cleaning of the inner surface of the nozzle: hereinafter to be also referred to as "final cleaning of nozzle") in CRP cell 19.

Conventionally, the CRP cell is used for the final nozzle cleaning to avoid contamination of specimens.

Among the three cells (CRP cell 19, WBC cell 27, RBC cell 28) in FIGS. 5(*a*), 5(*b*), and 6, the CRP cell has the least possibility of blood cells remaining. Since a specimen after lysis of all blood cells with a hemolysis reagent R1 is fed into the CRP cell, the possibility of blood cells remaining therein is close to none. On the contrary, red blood cells may remain in RBC cell, and not only white blood cells but also red blood cells may remain in the WBC cell also serving as a waste liquid chamber.

Therefore, in the apparatus of the above-mentioned patent document 1, the nozzle is finally cleaned after cleaning the inside of the CRP cell with a diluting liquid after completion of the CRP measurement. This step is as shown in the flow chart of FIG. 7 as steps a6-a8, where the CRP measurement and the final nozzle cleaning are serially performed.

In view of the apparatus for measuring blood cells and immunity from whole blood of the above-mentioned patent document 1, an apparatus added with exclusive measuring-cells has been further developed to enable the classification of white blood cells into 5 types. However, even in such an immunity measuring apparatus, final nozzle cleaning requires repeats of discharging and sucking and discharging of a clean diluting liquid into and from the CRP cell and, where necessary, the diluting liquid is discarded and a fresh diluting liquid needs to be used for the above repeats. The cleaning takes about 60 seconds.

Conventional apparatuses for measuring blood cells and immunity from whole blood, as shown in FIGS. 5(*a*), 5(*b*), and 6, require about 4 minutes of treatment time per one specimen. The processing time of about 4 minutes per one specimen as mentioned above is free of problems and preferable for general tests. However, in an institution where a large number of specimens need to be processed in one day, shortening of time even by several dozen seconds greatly contributes to an increase in the daily through-put.

On the contrary, in conventional apparatuses for measuring blood cells and immunity from whole blood, the moving speed and sucking and discharging speed of the sampling nozzle are appropriate, and each processing step is essential, and therefore, there is no room for reduction in reaction time of reagents, measurement time, cleaning frequency and the like.

Given the conventional constitution as mentioned above, the present invention proposes a configuration shown in FIG. 1, wherein an exclusive chamber A for the final cleaning of nozzle 36 (cleaning chamber for immunity measurement) is newly formed, and the final cleaning of nozzle 36 simultaneously proceeds in the cleaning chamber A while the CRP measurement is being performed in the CRP cell.

This configuration for simultaneous progress omits about 60 seconds necessary for the final nozzle cleaning, and the processing time for one specimen becomes about 3 minutes from the conventional 4 minutes or so.

The measurement processing time can be drastically shortened by the addition of the cleaning chamber A for immunity measurement and use thereof (final cleaning of the nozzle that simultaneously proceeds with the immunity measurement). In addition thereto, cleaning of a nozzle having blood (particularly blood cells) thereon can be completely separated from the cleaning of a nozzle having a liquid thereon, which liquid containing no residual blood (particularly blood cells) since it was mixed with a hemolysis reagent for immunity measurement. Thus, by performing the final cleaning in the cleaning chamber A for immunity measurement, contamination with other specimens can be eliminated more completely.

Moreover, since a cleaning chamber A for immunity measurement has been provided, not only the final nozzle cleaning but also the outer surface of the nozzle can be cleaned as appropriate after suction of various reagents relating to the immunity measurement, by using the cleaning chamber for immunity measurement.

The nozzle 36 is controlled by a computer to be cleaned on the outer surface and the inner surface thereof in the cleaning chamber for immunity measurement, while the immunity measurement is being performed in the immunity-measuring cell 19.

The cleaning chamber for immunity measurement may be any as long as it has a depth sufficient to receive the part of the nozzle to be immersed in the reagent and the like. While such depth varies depending on the nozzle, for example, it is preferably about 20 mm-80 mm.

The shape of the body of the cleaning chamber for immunity measurement is not particularly limited. However, a cylindrical shape is preferable since the liquid injected into the chamber does not remain but is completely discharged (from the aspect of liquid waste efficiency). When the body of the cleaning chamber for immunity measurement has a cylindrical shape, the inner diameter thereof is not particularly limited, and preferably about 10 mm-20 mm. When the inner diameter of the cleaning chamber for immunity measurement is excessively large, the consumption amount of the cleaning liquid becomes high, and a longer time is necessary for filling the chamber with a diluting liquid and the like for the cleaning to a predetermined level. Also, it is disadvantageous for the miniaturization of the apparatus and the like.

On the other hand, when the inner diameter is excessively small, a carriage (moving mechanism such as belt and the like) used for moving the nozzle in the horizontal direction is required to have high accuracy of the stop position, which in turn unpreferably increases the risk of damaging the nozzle and the cleaning chamber, and scattering of the diluting liquid due to a failure of the nozzle to descend into the chamber.

The material of the cleaning chamber for immunity measurement may be any as long as it has chemical resistance and processability and, for example, polyvinyl chloride (PVC), poly(ethylene terephthalate) (PET), polypropylene (PP) and the like can be mentioned. In view of cost and processability, PVC is a preferable material.

As shown in FIG. 1, the position of the cleaning chamber for immunity measurement is preferably next to the immunity-measuring cell (CRP cell) and between the blood cell counting-measuring cell and the immunity-measuring cell, since the movement of the nozzle can be minimized.

As shown in FIG. 1 with a broken line, an exhaust pipe similar to that in the CRP cell is connected to a lower end part of the cleaning chamber for immunity measurement, whereby the waste liquid is transferred to a waste liquid container 18 via an electromagnetic valve device 12 and a pump P.

The step of the final cleaning of the nozzle in the cleaning chamber for immunity measurement is the same as the cleaning conventionally performed in the CRP cell. To be specific, a predetermined amount of a clean diluting liquid is discharged in the chamber, and sucking and discharging of the diluting liquid is repeated (preferably about 2 or 3 repeats) to clean the inner surface of the nozzle. Where necessary, the used diluting liquid needs to be discarded and a fresh diluting liquid needs to be supplied to repeat the discharging and sucking. In a preferable embodiment, the diluting liquid is discarded once or twice. In this case, a nozzle cleaning device may be activated.

In addition, the nozzle after sucking reagents R1-R3 may be cleaned in the cleaning chamber for immunity measurement.

The diluting liquid may be any as long as it can be used for diluting a specimen for the measurement and a latex reagent (undiluted solution), such as physiological saline, phosphate buffer diluting liquid and the like.

The cleaning of the outer surface of a nozzle by a nozzle cleaning device, and the final cleaning of the nozzle in a cleaning chamber for immunity measurement may be performed using a diluting liquid alone.

The cleaning chamber for immunity measurement may be used, in addition to the final cleaning of the nozzle, as a receiving port for cleaning the outer surface of the nozzle by a nozzle cleaning device in the step of dispensing each reagent in the CRP cell. In other words, in the step for dispensing each reagent for immunity measurement, the nozzle may be moved to be right over the cleaning chamber for immunity measurement, and the nozzle cleaning device may be activated thereon.

Using the aforementioned configuration including a cleaning chamber for immunity measurement, the operating time can be advantageously shortened by parallel operation of the chamber drainage and reduction of the carriage travel distance.

In a preferable embodiment of the present invention, specimen cleaning chamber B is further provided as shown in FIG. 1. The specimen cleaning chamber exclusively cleans a nozzle after dispensation for counting and measuring the blood cells, which possibly has blood thereon.

The shape, size and material of the specimen cleaning chamber may be similar to those of the above-mentioned cleaning chamber for immunity measurement. A discharge pipe is connected to a lower end part of the specimen cleaning chamber, as shown in FIG. 1 with a broken line, whereby the waste liquid is transferred to a waste liquid container 18 via an electromagnetic valve device 12 and a pump P.

As shown in FIG. 1, by using the cleaning chamber for immunity measurement and the specimen cleaning chamber for different purposes, cleaning the nozzle free of possibility of blood adhesion in the cleaning chamber for immunity measurement, and cleaning the nozzle possibly having blood adhered thereon in the specimen cleaning chamber, the contamination between specimens can be prevented more completely, and the processing time for one specimen can be advantageously shortened by employing a parallel and simultaneous operation.

Figure 2:
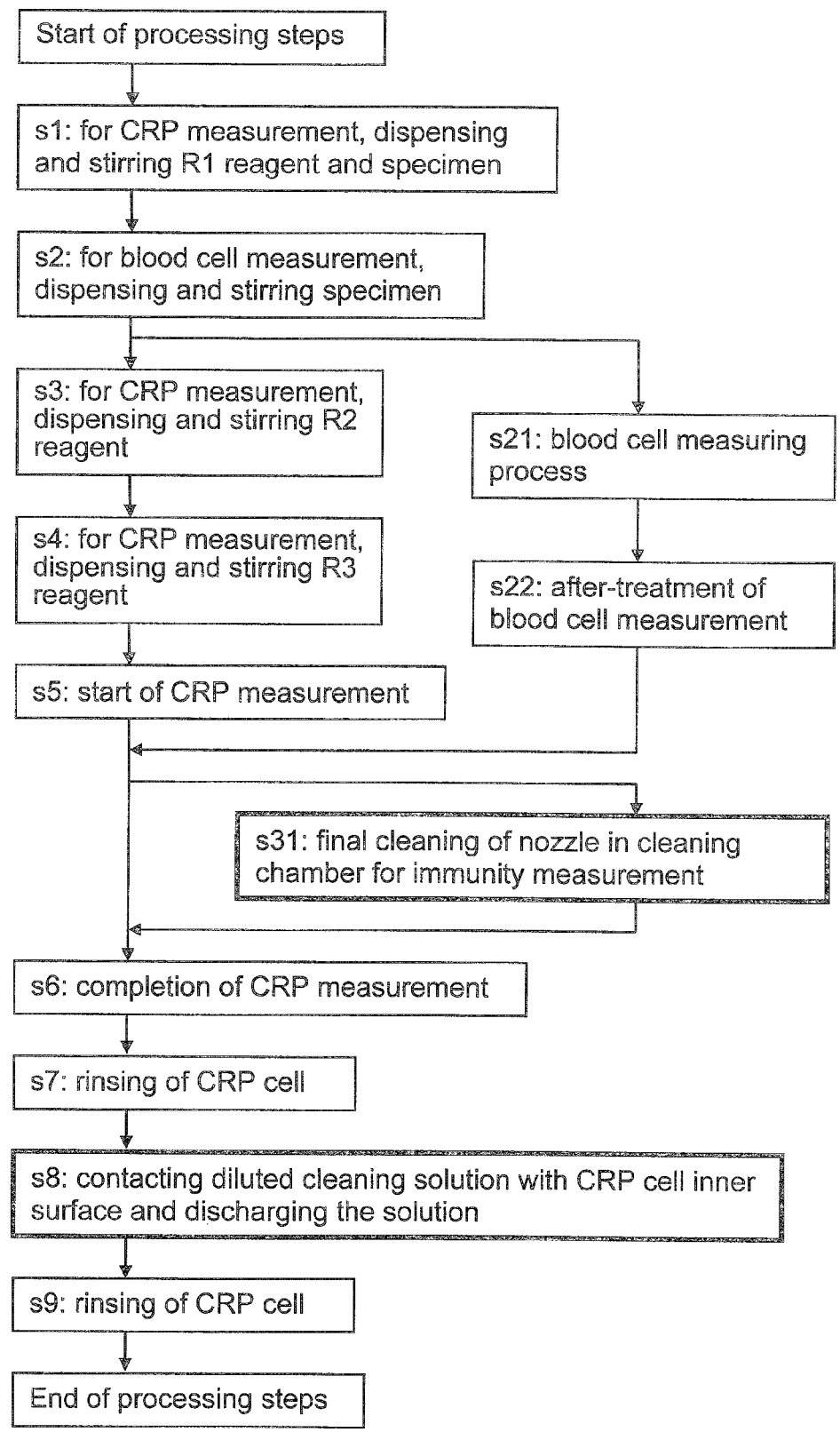
FIG. 2 is a flow chart showing the movement of the sampling nozzle in the preferable apparatus for measuring blood cells and immunity from whole blood of the present invention.

FIG. 2 is a flowchart showing one example of the sequential operation for cleaning the nozzle by cleaning chamber A for immunity measurement and specimen cleaning chamber B shown in FIG. 1.

The operation of each part of the apparatus involves, according to the commands previously determined by the control part (computer), moving the nozzle horizontally and vertically by a probe unit, and suction and discharge performed by an electromagnetic valve part. In the following explanation, except for an important movement, the nozzle behavior is described without detailed movements such as [upwardly moving from a certain position, horizontally moving, and downwardly moving to reach the next position] and the like, and simply expressed by [moving from a certain position to the next position].

First, when the processing step is started by turning on a start switch by a user, the nozzle starts the motion of step s1. The turning on operation of the start switch may be performed by any manner such as pressing a push button, a remote operation by communication with other computers and the like. For example, the operation of closing the lid of the specimen container set part C in FIG. 3 may also execute start switch ON.

(Step s1)

First, the nozzle 36 in the home position is activated to perform CRP measurement, moves to the R1 reagent container 20 and sucks R1 reagent.

After the suction, the nozzle moves to be above the cleaning chamber A for immunity measurement, and the outer surface thereof is cleaned by the nozzle cleaning device (the nozzle descends and ascends for cleaning).

Then, the nozzle moves to the specimen container 4, and sucks the specimen (whole blood) in the specimen container 4 for the CRP measurement.

Then, the nozzle moves to the specimen cleaning chamber B, and the outer surface thereof is cleaned by the nozzle cleaning device (the nozzle descends and ascends for cleaning).

Then, the nozzle moves to the CRP cell, and discharges the sucked specimen and the R1 reagent into the CRP cell. Thereafter, the liquid in the CRP cell is stirred by being repeatedly drawn and extruded by a quantitative discharging device 19e exemplarily shown as a preferable embodiment in FIG. 1 (electromagnetic selector valves 19c, 19d perform a switching action to produce the pipeline).

Then, the nozzle moves to the specimen cleaning chamber B, and the outer surface of the nozzle is cleaned by the nozzle cleaning device.

(Step s2)

The nozzle moves to the specimen container 4, and sucks the specimen (whole blood) in the specimen container 4 for counting-measuring the blood cells.

Then, the nozzle moves to the specimen cleaning chamber B, and the outer surface of the nozzle is cleaned by the nozzle cleaning device.

Then, the nozzle moves to WBC cell 27d, and dispenses the sucked specimen into the cell. At the same time, a diluting liquid is injected into the cell from the piping (not shown) connected to the side surface of the cell, and air is discharged by a pump (not shown) from the piping (not shown), which is connected to the lower part of the cell, to stir the inside of the cell.

Then, the nozzle moves to BASO cell 27a, and dispenses the sucked specimen into the cell. At the same time, a basophil hemolysis agent is injected into the cell from the piping (not shown) connected to the side face of the cell, and air is discharged by a pump (not shown) from the piping (not shown), which is connected to the lower part of the cell, to stir the inside of the cell.

Then, the nozzle moves to the LMNE cell 27b, and dispenses the sucked specimen into the cell. At the same time, an eosinophil measurement reagent is injected into the cell from the piping (not shown) connected to the side face of the cell, and air is discharged by a pump (not shown) from the piping (not shown), which is connected to the lower part of the cell, to stir the inside of the cell.

Then, the nozzle moves to the specimen cleaning chamber B, and the inner surface and outer surface of the nozzle are cleaned by the nozzle cleaning device.

A part of the specimen liquid diluted in the WBC cell 27*d* in the above-mentioned step s2 is transferred to RBC cell 27*c*, the diluting liquid is injected into the cell from the piping (not shown) connected to the RBC cell and, in the same manner as above, air is discharged to stir the inside of the cell, whereby the dilution is completed. Thereafter, a hemoglobin hemolysis reagent is injected into the WBC cell and, in the same manner as above, air is discharged to stir the inside of the cell, whereby the specimen is lysed. In addition, the diluting agent is injected into the LMNE cell from the piping (not shown) connected to the cell and, in the same manner as above, air is discharged to stir the inside of the cell, whereby the dilution is completed.

(Step s21)

In the BASO cell 27*a*, a specimen liquid passes through a device for performing the electric resistance method, which is formed on the lower part, whereby basophils are counted.

In the LMNE cell 27*b*, a specimen liquid passes through a device for performing a light-focused flow impedance method, which is formed on the upper part, whereby each volume and each absorbance of lymphocytes (L), monocytes (M), neutrophils (N) and eosinophils (E) are measured. The measurement data are transmitted to the control part, and processed for counting-measuring the cells for the classification into 4 types by the LMNE matrix and the like.

In the RBC cell 27*c*, a specimen liquid passes through the device for the electric resistance method, which is formed on the lower part, whereby the red blood cells and platelets are measured for the number and volume.

In the WBC cell 27*d*, the hemoglobin concentration is measured by an optical device for performing absorption spectrophotometry by colorimetry (non-cyanogen method). In addition, a specimen passes through the device for performing the electric resistance method, which is formed on the lower part, and the number of white blood cells is measured. The measurement data are transmitted to the control part, and processed for frequency distribution.

(Step s22)

For an after-treatment of the measurement in the BASO cell 27*a*, the nozzle moves to the BASO cell, and a diluting liquid is injected into the cell from the nozzle cleaning device.

(Step s3)

In parallel with the treatment in step s21, the nozzle moves to the R2 reagent container for the CRP measurement, and sucks R2 reagent.

Then, the nozzle moves to be above the cleaning chamber A for immunity measurement, and the outer surface of the nozzle is cleaned by the nozzle cleaning device.

Then, the nozzle moves to the CRP cell, and discharges the sucked R2 reagent into the CRP cell.

Then, the nozzle moves to be above the cleaning chamber A for immunity measurement, and the outer surface of the nozzle is cleaned by the nozzle cleaning device.

(Step s4)

Then, the nozzle moves to the R3 reagent container for the CRP measurement, and sucks R3 reagent.

Then, the nozzle moves to be above the cleaning chamber A for immunity measurement, and the outer surface of the nozzle is cleaned by the nozzle cleaning device.

Then, the nozzle moves to the CRP cell, and discharges the sucked R3 reagent into the CRP cell.

Then, the nozzle moves to be above the cleaning chamber A for immunity measurement so as to be cleaned in step s31 mentioned below.

(Step s5)

The CRP measurement in the CRP cell is started. The processing time until completion of the measurement is about 60 seconds.

(Step s31)

When the CRP measurement in the CRP cell is started, the nozzle moves to the inside of the cleaning chamber A for immunity measurement, and the inner surface and outer surface of the nozzle are sufficiently cleaned with a diluting liquid. In this step, discharging the diluting liquid, sucking and discharging the same into the cleaning chamber A for immunity measurement is repeated. Where necessary, the diluting liquid is discarded, and a fresh diluting liquid is used to repeat the discharging, sucking and discharging again of the diluting liquid.

(Step s6)-(Step s7)

When the final cleaning of the nozzle is completed and the CRP measurement in step s6 is completed, the nozzle moves to the CRP cell. At step s7, the inside of the CRP cell is cleaned with a diluting liquid.

(Step s8)-(Step s9)-Completion of Treatment Steps

When the cleaning of the inside of the CRP cell with a diluting liquid is completed, a predetermined amount of a diluting liquid is injected into the CRP cell from the nozzle cleaning device in step s8. Then, an electromagnetic selector valve is activated, a cleaning solution is injected into the CRP cell to a defined liquid surface level to produce a diluted cleaning solution, after which it is maintained for a predetermined time and quickly discharged.

Then at step s9, the inside of the CRP cell is rinsed with the diluting liquid, and the processing steps are completed.

As explained above by referring to the flow chart of FIG. 2, in the present invention, in the final stage of immunity measurement treatment of one specimen, a diluting liquid is injected into the CRP cell and then a cleaning solution is injected, and the produced diluted cleaning solution is brought into contact with the inner wall surface of the CRP cell. As a result, the interval of the routine cleanings is drastically elongated and, in a preferable embodiment, routine cleanings becomes unnecessary.

Furthermore, a cleaning chamber for immunity measurement is newly provided, a specimen cleaning chamber is further provided, and they are controlled to be used completely differently depending on the presence or absence of blood adhered thereto. Therefore, the cleaning chamber for immunity measurement has a sufficiently small possibility of contamination with blood. Moreover, the final cleaning of the nozzle, which takes a sufficiently long time in the cleaning chamber for immunity measurement, does not influence the whole processing steps.

Experimental Example

Using an apparatus having the constitution shown in FIG. 1 and according to the flow shown in FIG. 2, a cleaning solution was reacted on the inner wall surface of a CRP cell at the end of the measurement of every specimen, the blank absorbance in the CRP measurement of each specimen was measured, and the degree of change thereof was examined.

The R3 reagent used was the R3 reagent in BLOIM-MUKIT CRP (manufactured by HORIBA, Ltd.), which was a reagent containing latex (polystyrene particles) sensitized with anti-human CRP polyclonal antibody (rabbit).

The cleaning solution used was a cleaning solution containing 0.25 wt % of Brij (polyoxyethylenelauryl ether) as a main surfactant and 0.5 wt % of Savinase as an enzyme.

When the cleaning solution was injected into the CRP cell, it was diluted by first injecting a diluting liquid (diluent). The mixing ratio of the cleaning solution and the diluting liquid was 4:5 in volume ratio (concentration of the cleaning solution in the diluted cleaning solution was about 45 wt %).

The injection time of the cleaning solution was 1 second, the maintenance time was 2 seconds and the discharge time was 1 second.

Figure 4:
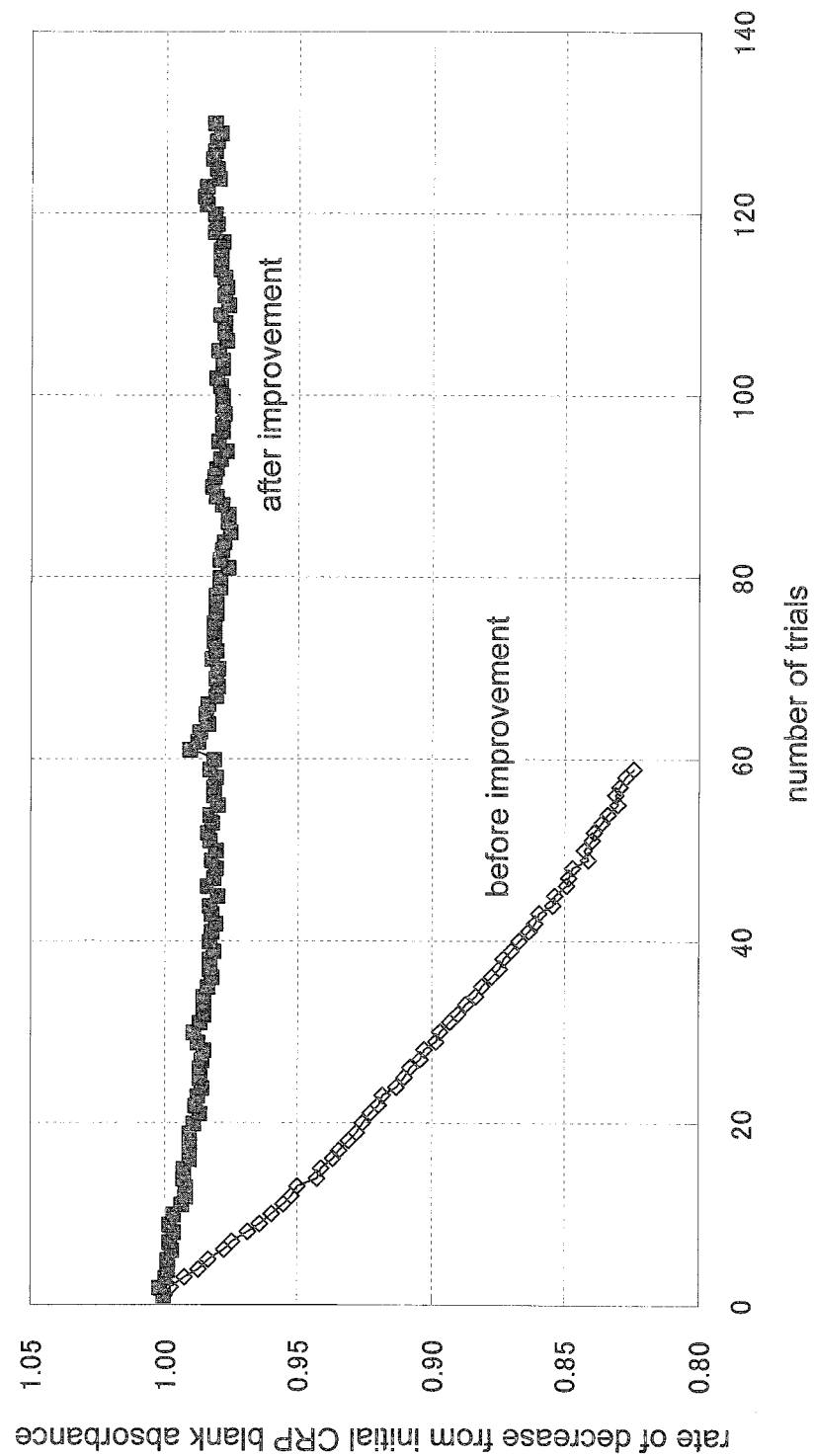
FIG. 4 is a graph showing the difference between injection of a cleaning solution into the CRP cell (the present invention) and rinsing with a diluting liquid alone (conventional example). The vertical axis of the graph shows the ratio of the blank absorbance in the measurement of the second specimen and thereafter relative to the blank absorbance in the measurement of the first specimen as 1, and the horizontal axis of the graph shows the number of specimens (number of measurements performed).

The ratio of the blank absorbance in the measurement of the second specimen and thereafter relative to the blank absorbance in the measurement of the first specimen as 1 is plotted in the graph of FIG. 4 as a black square mark.

As is clear from the graph of this Figure, the blank absorbance did not show a remarkable decrease as compared to the blank absorbance in the measurement of the first specimen, and routine cleaning was not necessary even after exceeding the specimen number of 100.

In addition, it was also clarified that a false low value caused by excessive removal of the latex particles did not occur.

Comparative Example

Under the exactly same conditions as in the above-mentioned Experimental Example except that the final cleaning of the CRP cell in the measurement of one specimen was performed only with a diluting liquid as in the conventional methods, the blank absorbance in the CRP measurement of each specimen was measured, and the degree of change thereof was examined.

The CRP cell was cleaned with a diluting liquid following the conventional, general cleaning method, and a diluting liquid was injected from above the cell and discharged. This simple cleaning was repeated twice.

In the same manner as in the above-mentioned Experimental Example, the ratio of the blank absorbance in the measurement of the second specimen and thereafter relative to the blank absorbance in the measurement of the first specimen as 1 is plotted in the graph of FIG. 4 as a white rhombus mark.

As is clear from the graph of this Figure, the blank absorbance markedly decreased as compared to the blank absorbance in the measurement of the first specimen, and routine cleaning was necessary.

INDUSTRIAL APPLICABILITY

According to the present invention, the development of a false low value caused by excessive removal of latex particles can be suppressed, deposition of the latex particles can be suppressed, and therefore, the interval of the routine cleanings of the CRP cell can be increased and routine cleanings can be eliminated.

The present invention can drastically shorten the measurement processing time necessary for one specimen while maintaining all conventional processing steps, by performing a parallel and simultaneous processing of the final cleaning of the nozzle by a cleaning chamber for immunity measurement, which is a preferable embodiment of the present invention.

Consequently, a preferable apparatus for measuring blood cells and immunity from whole blood can be provided to medical institutions and the like where a large number of specimens are measured.

This application is based on patent application No. 2013-104028 filed in Japan, the contents of which are incorporated in full herein.

The invention claimed is:

1. An apparatus for measuring blood cells and immunity from whole blood and performing an immunity measurement in an immunity measuring cell and counting and measuring of blood cells is performed in blood cell counting-measuring cell(s), comprising:
   an immunity measuring part comprising the immunity measuring cell;
   a reagent container containing a latex reagent for the immunity measurement;
   reagent container(s) containing other necessary reagent(s) for the immunity measurement;
   a blood cell counting-measuring part comprising the blood cell counting-measuring cell(s);
   wherein the immunity measuring part, the reagent container(s) and the blood cell counting-measuring part are placed at predetermined positions, and
   a controller programmed to control a single sampling nozzle to move to the predetermined positions to suck and discharge a specimen and the reagent(s), and control the immunity measuring cell to perform an immunity measurement, and control the blood cell counting-measuring cell(s) to perform counting and measuring of the blood cells,
   a cleaning solution tank containing a cleaning solution and a cleaning agent for the aforementioned latex reagent;
   wherein the controller is further programmed to, every time immunity measurement of one specimen is completed in the immunity measuring cell and the specimen is discharged, control an injecting device to first inject a predetermined amount of a diluting liquid into the immunity measuring cell and then to inject a predetermined amount of the cleaning solution into the immunity measuring cell, whereby the cleaning solution diluted to a predetermined concentration contacts an inner wall surface of the immunity measuring cell, and then, control the immunity measuring cell to discharge the diluted cleaning solution.

2. The apparatus for measuring blood cells and immunity from whole blood according to claim 1, wherein a bottom part of the immunity measuring cell is provided with a discharge port for discharging a liquid in the cell, and electromagnetic selector valve(s) is(are) connected to the discharge port, and
   the controller is further programmed to control operation of the electromagnetic selector valve to inject the above-mentioned cleaning solution into the immunity measuring cell through the discharge port.

3. The apparatus for measuring blood cells and immunity from whole blood according to claim 2, wherein the controller is further programmed to control the electromagnetic selector valve to inject the entire amount of the above-mentioned cleaning solution in a plurality of divided portions into the immunity measuring cell a plurality of times.

4. The apparatus for measuring blood cells and immunity from whole blood according to claim 1, further comprising:
   a sampling nozzle cleaning device accompanying the sampling nozzle, discharging a diluting liquid to clean the outer surface of the nozzle with the diluting liquid.

5. The apparatus for measuring blood cells and immunity from whole blood according to claim 1, wherein the controller is further programmed to:

control the injecting device to inject the above-mentioned cleaning solution in 3 seconds or less into the immunity measuring cell in which the predetermined amount of the diluting liquid has been injected;

then control the injecting valve to inject the above-mentioned cleaning solution diluted to the predetermined concentration to maintain contact with the inner wall surface of the immunity measuring cell for 1-5 seconds; and then control the immunity measuring cell to discharge the aforementioned diluted cleaning solution in 3 seconds or less.

\* \* \* \* \*